(12) United States Patent
Prince

(10) Patent No.: US 8,190,236 B2
(45) Date of Patent: May 29, 2012

(54) TOURNIQUET FOR MAGNETIC RESONANCE ANGIOGRAPHY, AND METHOD OF USING SAME

(76) Inventor: Martin R. Prince, New York, NY (US)

( * ) Notice: Subject to any disclaimer, the term of this patent is extended or adjusted under 35 U.S.C. 154(b) by 1839 days.

(21) Appl. No.: 11/331,519

(22) Filed: Jan. 13, 2006

(65) Prior Publication Data

US 2006/0167492 A1 Jul. 27, 2006

Related U.S. Application Data

(60) Provisional application No. 60/646,434, filed on Jan. 24, 2005, provisional application No. 60/678,410, filed on May 6, 2005.

(51) Int. Cl.
*A61B 5/055* (2006.01)
(52) U.S. Cl. .......... 600/421; 600/415; 600/420
(58) Field of Classification Search .......... 600/410–411, 600/415, 419–422; 128/653.2–653.5; 324/306–309, 324/318, 322; 606/201–204, 213
See application file for complete search history.

(56) References Cited

U.S. PATENT DOCUMENTS

| | | | |
|---|---|---|---|
| 2,823,668 A * | 2/1958 | Court et al. ............. 602/13 |
| 3,467,077 A * | 9/1969 | Cohen ................ 600/499 |
| 3,654,931 A * | 4/1972 | Hazlewood ............ 606/202 |
| 3,760,795 A | 9/1973 | Adelhed |
| 4,207,875 A | 6/1980 | Arkans |
| 4,207,876 A | 6/1980 | Annis |
| 4,320,746 A | 3/1982 | Arkans et al. |
| 4,402,312 A | 9/1983 | Villari et al. |
| 4,635,635 A * | 1/1987 | Robinette-Lehman ....... 606/202 |
| 4,791,372 A * | 12/1988 | Kirk et al. ............... 324/318 |
| 5,048,536 A | 9/1991 | McEwen |

(Continued)

FOREIGN PATENT DOCUMENTS

GB 1400957 A 7/1975
(Continued)

OTHER PUBLICATIONS

Zhang et al., "Decreased venous contamination on 3D gadolinium-enhanced bolus chase peripheral MR angiography using thigh compression", A JR 2004; 183:1041-7.*

(Continued)

*Primary Examiner* — Long V. Le
*Assistant Examiner* — Angela M Hoffa
(74) *Attorney, Agent, or Firm* — Scott E. Kamholz; Peter K. Sollins; Foley Hoag LLP

(57) ABSTRACT

There are many inventions described herein as well as many aspects and embodiments of those inventions. A thigh compression device and technique to control, time, delay and/or prevent excessive early venous enhancement relative to arterial enhancement and thereby improve and/or enhance MRA images, including peripheral MRA images. In one embodiment, the present invention uses a curved strip of material which is longer on the superior edge and shorter along the inferior edge. When wrapped around the conical or conal-like shape of the thigh of a subject (for example, a human), the thigh compression device more uniformly conforms to and/or fits around the thigh, providing more even/uniform compression as well as reducing, minimizing and/or eliminating significant movement of the thigh compression device towards the knees of the subject. Notably, a snug fit on the thighs may also enable the thigh compression device to be inflated with less fluid (for example, air) which is faster and less cumbersome for the operator.

28 Claims, 13 Drawing Sheets

U.S. PATENT DOCUMENTS

| | | | |
|---|---|---|---|
| 5,193,549 A | 3/1993 | Bellin et al. | |
| 5,368,547 A * | 11/1994 | Polando | 601/151 |
| 5,383,919 A | 1/1995 | Kelly et al. | |
| 5,400,787 A * | 3/1995 | Marandos | 600/422 |
| 5,407,421 A | 4/1995 | Goldsmith | |
| 5,413,582 A * | 5/1995 | Eaton | 606/202 |
| 5,466,250 A * | 11/1995 | Johnson et al. | 607/104 |
| 5,543,710 A * | 8/1996 | Jones | 324/318 |
| D376,013 S * | 11/1996 | Sandman et al. | D24/169 |
| 5,590,654 A | 1/1997 | Prince | |
| 5,607,447 A * | 3/1997 | McEwen et al. | 606/207 |
| 5,690,672 A * | 11/1997 | Cohen | 606/203 |
| 5,706,813 A * | 1/1998 | Filler et al. | 600/422 |
| 5,741,295 A * | 4/1998 | McEwen | 606/202 |
| 5,792,056 A | 8/1998 | Prince | |
| 5,795,312 A * | 8/1998 | Dye | 601/151 |
| 5,827,187 A * | 10/1998 | Wang et al. | 600/419 |
| 5,836,878 A * | 11/1998 | Mock et al. | 600/415 |
| 5,924,987 A | 7/1999 | Meaney et al. | |
| 6,007,559 A * | 12/1999 | Arkans | 606/201 |
| 6,178,340 B1 * | 1/2001 | Svetliza | 600/310 |
| 6,230,040 B1 | 5/2001 | Wang et al. | |
| 6,240,311 B1 | 5/2001 | Prince | |
| 6,245,023 B1 * | 6/2001 | Clemmons | 600/499 |
| 6,311,085 B1 | 10/2001 | Meaney et al. | |
| 6,375,620 B1 * | 4/2002 | Oser et al. | 600/481 |
| 6,438,402 B1 * | 8/2002 | Hashoian et al. | 600/410 |
| 6,440,093 B1 * | 8/2002 | McEwen et al. | 601/150 |
| 6,445,945 B1 * | 9/2002 | Arsenault | 600/431 |
| 6,463,309 B1 * | 10/2002 | Ilia | 600/310 |
| 6,463,318 B2 | 10/2002 | Prince | |
| 6,564,085 B2 | 5/2003 | Meaney et al. | |
| 6,577,887 B2 * | 6/2003 | Wolff et al. | 600/411 |
| 6,578,428 B1 * | 6/2003 | Dromms et al. | 73/729.2 |
| 6,682,547 B2 * | 1/2004 | McEwen et al. | 606/202 |
| 6,684,096 B2 * | 1/2004 | Schmit et al. | 600/415 |
| 6,741,881 B2 | 5/2004 | Prince | |
| 6,746,470 B2 * | 6/2004 | McEwen et al. | 606/202 |
| 6,754,521 B2 | 6/2004 | Prince | |
| 6,879,853 B2 | 4/2005 | Meaney et al. | |
| 6,882,878 B2 * | 4/2005 | Schmit et al. | 600/415 |
| 7,306,568 B2 * | 12/2007 | Diana | 601/15 |
| 7,326,227 B2 * | 2/2008 | Dedo et al. | 606/203 |
| 7,331,977 B2 * | 2/2008 | McEwen et al. | 606/202 |
| 7,384,425 B2 * | 6/2008 | McEwen | 606/201 |
| 2002/0173718 A1 * | 11/2002 | Frisch et al. | 600/424 |
| 2003/0036771 A1 * | 2/2003 | McEwen et al. | 606/202 |
| 2003/0167070 A1 * | 9/2003 | McEwen et al. | 606/203 |
| 2004/0040064 A1 * | 3/2004 | Mah et al. | 2/2.14 |
| 2004/0133135 A1 * | 7/2004 | Diana | 601/152 |
| 2004/0210176 A1 * | 10/2004 | Diana | 601/151 |
| 2005/0144810 A1 * | 7/2005 | Marvin et al. | 36/93 |
| 2005/0159690 A1 * | 7/2005 | Barak et al. | 601/149 |
| 2005/0187503 A1 * | 8/2005 | Tordella et al. | 602/13 |
| 2006/0048415 A1 * | 3/2006 | Marvin et al. | 36/93 |
| 2006/0112593 A1 * | 6/2006 | Marvin et al. | 36/29 |
| 2006/0130370 A1 * | 6/2006 | Marvin et al. | 36/93 |
| 2006/0147492 A1 * | 7/2006 | Hunter et al. | 424/426 |
| 2006/0162186 A1 * | 7/2006 | Marvin et al. | 36/45 |
| 2006/0173278 A1 * | 8/2006 | Wahl et al. | 600/410 |
| 2008/0082029 A1 * | 4/2008 | Diana | 601/152 |

FOREIGN PATENT DOCUMENTS

| | | |
|---|---|---|
| WO | WO-99/63892 | 12/1999 |

OTHER PUBLICATIONS

Lee et al., "Distal lower extremity arteries: evaluation with two-dimensional MR digital subtraction angiography", Radiology. May 1998, 207(2):505-12.

Maki et al., "Utilizing SENSE to achieve lower station sub-millimeter isotropic resolution and minimal venous enhancement in peripheral MR angiography", JMRI, Apr. 2002, 15(4):484-91.

Foo et al., "High-spatial-resolution multistation MR imaging of lower-extremity peripheral vasculature with segmented volume acquisition: feasibility study", Radiology Jun. 2001, 219(3):835-41.

Leiner et al., "Three-dimensional contrast-enhanced moving-bed infusion-tracking (MoBi-track) peripheral MR angiography with flexible choice of imaging parameters for each field of view" JMRI, Apr. 2000, 11(4):368-77.

Wentz et al., "High-resolution magnetic resonance angiography of hands with timed arterial compression (tac-MRA)" Lancet 2003, 36149-50.

Vogt et al., "Venous compression at high-spatial resolution-resolution three-dimensional MR angiography of peripheral arteries", Radiology 2004, 233:913-20.

Herborn et al., "Peripheral vasculature: whole body MR angiography with midfemoral venous compression—initial experience", Radiology 2004, 230:872-8.

Bilecen et al., "Infragenual calf-compression for reducing venous contamination in contrast-enhanced MR angiography of the calf", JMRI 2004, Aug, 20(2):347-51.

Bilecen et al., "Optimized assessment of hand vascularization on contrast-enhanced MR angiography with a subsystolic continuous compression technique" AJR, 2004; 182:180-2.

Zhang et al., "Decreased venous contamination on 3D gadolinium-enhanced bolus chase peripheral MR angiography using thigh compression", AJR 2004; 183:1041-7).

European Written Opinion and Search Report for EP09176780 dated Dec. 9, 2009.

* cited by examiner

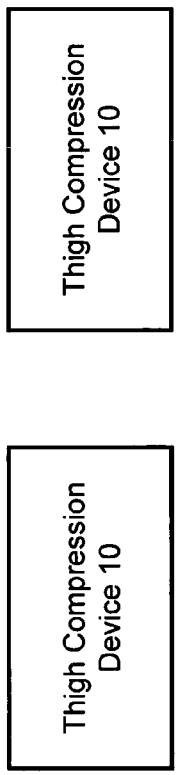

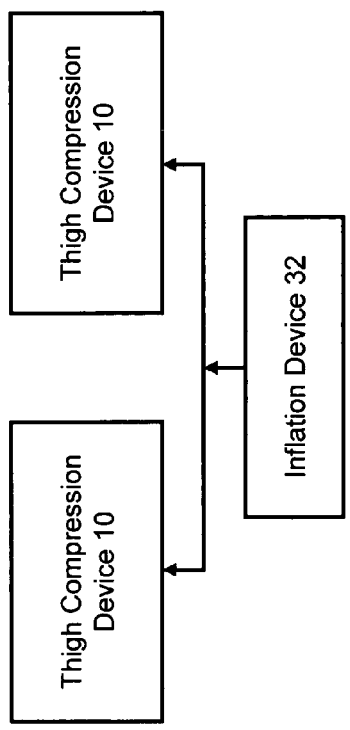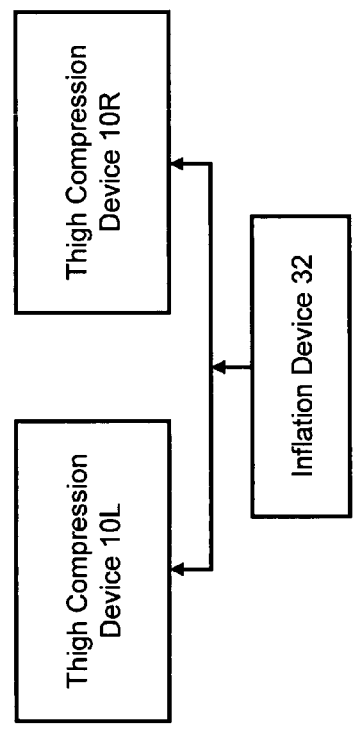

TOURNIQUET FOR MAGNETIC RESONANCE ANGIOGRAPHY, AND METHOD OF USING SAME

CROSS-REFERENCE TO RELATED APPLICATIONS

This application claims priority to: (1) U.S. Provisional Application Ser. No. 60/646,434, entitled "Tourniquet for Magnetic Resonance Angiography, and Method of Using Same", filed Jan. 24, 2005; and (2) U.S. Provisional Application Ser. No. 60/678,410, entitled "Tourniquet for Magnetic Resonance Angiography, and Method of Using Same", filed May 6, 2005 (hereinafter collectively "the Provisional Applications"). The contents of the Provisional Applications are incorporated by reference herein in their entirety.

BACKGROUND

This invention relates to a device to improve the images obtained using magnetic resonance angiography ("MRA"); and more particularly, in one aspect, to a device (as well as a method of using the device) that selectively compresses veins relative to arteries to control, time, delay and/or prevent excessive early venous enhancement relative to arterial enhancement and thereby improve and/or enhance MRA images.

Moving table MRA, sometimes known as bolus chase MRA, has had a revolutionary affect on imaging of the peripheral vasculature. Moving table MRA allows rapid imaging from the aorta to the feet, using one injection of a magnetic resonance ("MR") contrast agent (for example, gadolinium), often within a few minutes. In operation, the patient is advanced, between discrete imaging stations, through the MR scanner as the bolus of MR contrast agent flows down the torso and legs. In this way, one bolus of MR contrast agent is "shared" among multiple imaging stations covering the peripheral arteries or it can be extended to cover the arteries of the entire body. Moving table MRA is described in U.S. Pat. No. 5,924,987, which is incorporated by reference herein.

However, in many patients, the MR contrast agent bolus may "travel" down the legs at a rate that makes it difficult for the MR scanner to adequately, fully and/or optimally image the patient at and move between the plurality of imaging stations. In this instance, sometimes referred to as fast flow, the bolus is not optimally "shared" among the imaging stations and enhancement of veins may occur or result in the more distal stations thereby interfering with visualization of the arteries in the subsequent images.

Such venous enhancement may be referred to as venous contamination and may occur in up to 50% of patients. Notably, it is particularly common in diabetic patients and patients who have cellulitis or foot ulcers. These are the very patients in whom obtaining high resolution peripheral MR angiograms may be critical.

There are many conventional techniques to suppress venous contamination. (See, for example, (1) Lee et al., "Distal lower extremity arteries: evaluation with two-dimensional MR digital subtraction angiography", Radiology. 1998 May, 207(2):505-12; (2) Maki et al., "Utilizing SENSE to achieve lower station sub-millimeter isotropic resolution and minimal venous enhancement in peripheral MR angiography", JMRI, April 2002, 15(4):484-91; (3) Ho et al., "High-spatial-resolution multistation MR imaging of lower-extremity peripheral vasculature with segmented volume acquisition: feasibility study", Radiology June 2001, 219(3):835-41; (4) Leiner et al., "Three-dimensional contrast-enhanced moving-bed infusion-tracking (MoBi-track) peripheral MR angiography with flexible choice of imaging parameters for each field of view" JMRI, April 2000, 11 (4):368-77; (5) Wentz et al., "High-resolution magnetic resonance angiography of hands with timed arterial compression (tac-MRA)" Lancet 2003, 36149-50; (6) Vogt et al., "Venous compression at high-spatial resolution-resolution three-dimensional MR angiography of peripheral arteries", Radiology 2004, 233:913-20; (7) Herborn et al., "Peripheral vasculature: whole body MR angiography with midfemoral venous compression—initial experience", Radiology 2004, 230:872-8; (8) Bilicen et al., "Infragenual calf-compression for reducing venous contamination in contrast-enhanced MR angiography of the calf", JMRI August, 2004 20(2):347-51, (9) Bilicen et al., "Optimized assessment of hand vascularization on contrast-enhanced MR angiography with a subsystolic continuous compression technique" AJR, 2004;182:180-2; and (10) Zhang et al., "Decreased venous contamination on 3D gadolinium-enhanced bolus chase peripheral MR angiography using thigh compression", AJR 2004;183:1041-7).

Certain conventional techniques to suppress venous contamination employ faster imaging and/or faster table movement. An inherent problem with imaging faster to keep up with the bolus is that imaging faster reduces the time available for data acquisition. The result is that the final MR angiograms or images tend to have lower quality with lower resolution and less signal-to-noise ("SNR"). In addition, it may take time for the arteries distal to occlusive disease to fill in with the MR contrast agent to be adequately visualized. Notably, it is generally better to image longer for better filling of slowly filling arteries, higher resolution and greater SNR.

Drs. Meaney and Prince, in U.S. Pat. No. 5,924,967 (incorporated herein by reference), describe a number of techniques to suppress venous contamination. One such technique employs tourniquets to "slow down" blood flow and suppress venous enhancement. In this regard, the tourniquet is placed tight enough to compress veins, but not too tight because compressing arteries is undesirable. In general, compressed arteries may provide a false appearance of stenosis or occlusion if it is within the field of view of the MRA image. Notably, compressing an artery may be acceptable particularly if it is outside the field of view or already known to be free of significant disease.

Generally, tourniquets slow blood flow in and near the location around which the tourniquet is applied. In addition, where a tourniquet is applied to compress only veins, the more peripheral veins may become distended with blood. Thus, by placing or applying the tourniquet prior to injecting the MR contrast agent, the blood distending the veins is likely to be free of MR contrast agent. Once the MR contrast agent is injected, it flows down the arteries at high concentration, but then is rapidly diluted upon entering the dilated veins. This effect may reduce venous enhancement. It is especially helpful for the calf which commonly has venous enhancement if the gadolinium flows down the legs faster than the MR scanner table is advanced. Compression of veins also causes blood to back up and thereby slows down the arterial flow as well. Generally, the amount of compression obtained from typical elastic tourniquets is difficult to control and reproduce, which has a tendency to limit widespread applicability of the technique.

There is a need for, among other things, a thigh compression device and technique which may apply even or uniform (or substantially even or uniform) pressure "high" on the thigh. In addition, there is a need for a thigh compression device that fits and/or conforms to, the cone-like shape of the thigh, in order to limit, reduce and/or eliminate detrimental movement of the device. Moreover, there is a need for a thigh compression device and technique that (i) limits, reduces and/or eliminates the tendency to move, create motion or misregistration artifact, (ii) is relatively easy to operate or implement from outside the MR scanner and/or (iii) limits, reduces and/or eliminates "kinking" or "entanglement" of tubing (for example, via the MR scanner or other medical equipment) that is used to operate or implement the device. There is also a need for a thigh compression device that is easily and rapidly inflated and stays inflated in spite of leaks.

SUMMARY OF THE INVENTIONS

There are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

In one aspect, the present inventions are directed to a thigh compression device for use with magnetic resonance imaging equipment. The thigh compression device comprises a bladder pouch having a curved rectangular-like shape wherein the pouch includes first side that is longer than an opposing second side. An inflatable bladder, adapted to be inflated (to a pressure of greater than about 40 mm Hg) by a fluid (for example, a gas or liquid), is disposed within the bladder pouch. The thigh compression device further includes extension tubing coupled to the inflatable bladder as well as an attachment mechanism to secure the bladder pouch and the inflatable bladder to a thigh of a human, wherein when the thigh compression device is affixed on the thigh of the human using the attachment mechanism, the bladder pouch and the inflatable bladder conform to the conical shape of the thigh.

In one embodiment of this aspect of the present inventions, the thigh compression device includes a length of the first side of the bladder pouch which is greater than about 20 inches and less than about 50 inches. In another embodiment the bladder pouch includes third and fourth sides having a substantially equal length. The length of the third and fourth sides of the bladder pouch may be greater than about 4 inches and less than about 12 inches.

The bladder pouch may include a radius of curvature between 2 and 20 feet.

The thigh compression device may include an inflation device, coupled to the extension tubing, to inflate the inflatable bladder. The thigh compression device may also include a pressure gauge, coupled to the extension tubing or inflatable bladder, to provide information which is representative of the pressure of the fluid in the inflatable bladder.

In another principal aspect, the present inventions are directed to a thigh compression system for use with magnetic resonance imaging equipment. The thigh compression system includes first and second thigh compression devices. The first thigh compression device comprises: (1) a bladder pouch having a curved rectangular-like shape wherein the pouch includes first side that is longer than an opposing second side, (2) an inflatable bladder, adapted to be inflated (for example, to a pressure of greater than about 40 mm Hg) by a fluid (for example, a gas or liquid), disposed within the bladder pouch, (3) extension tubing coupled to the inflatable bladder, and (4) an attachment mechanism to secure the bladder pouch and the inflatable bladder to a right thigh of a human, wherein when the thigh compression device is affixed on the right thigh of the human using the attachment mechanism, the bladder pouch and the inflatable bladder conform to the conical shape of the right thigh.

The second thigh compression device comprises: (1) a bladder pouch having a curved rectangular-like shape wherein the pouch includes first side that is longer than an opposing second side, (2) an inflatable bladder, adapted to be inflated (for example, to a pressure of greater than about 40 mm Hg) by a fluid (for example, a gas or liquid), disposed within the bladder pouch, (3) extension tubing coupled to the inflatable bladder, and (4) an attachment mechanism to secure the bladder pouch and the inflatable bladder of the second thigh compression device to a left thigh of a human, wherein when the thigh compression device is affixed on the left thigh of the human using the attachment mechanism, the bladder pouch and the inflatable bladder conform to the conical shape of the left thigh.

The thigh compression system of this aspect of the inventions also includes an inflation device, coupled to the extension tubing of the first and second thigh compression devices, to simultaneously inflate the inflatable bladder of each of the first and second thigh compression devices.

In one embodiment, the length of the third and fourth sides of the bladder pouch of each of the first and second thigh compression devices may be greater than about 4 inches and less than about 12 inches.

The bladder pouch of each of the first and second thigh compression devices, in one embodiment, may include a radius of curvature between 2 and 20 feet.

The thigh compression system of this aspect of the inventions may also include a pressure gauge, coupled to the inflation device, to provide information which is representative of the pressure of the fluid in the inflatable bladder of each of the first and second thigh compression devices.

In yet another principal aspect, the present inventions are directed to a thigh compression system for use with magnetic resonance imaging equipment. The thigh compression system of this aspect of the inventions includes a thigh compression device including first and second layers of flexible material welded together to form an air tight bladder, wherein the bladder has a curved rectangular-like shape including a first side that is longer than an opposing second side, and wherein the bladder is inflatable by a fluid. The thigh compression device further includes multiple welds within the bladder which restrict the amount that the bladder expands when inflated. The thigh compression system further includes extension tubing coupled to the bladder, and an inflation device, coupled to the extension tubing of the thigh compression device, to inflate the inflatable bladder.

In one embodiment, the length of a first side of the thigh compression device is greater than about 20 inches and less than about 50 inches. In another embodiment, the bladder of the thigh compression device includes a radius of curvature between 2 and 20 feet. Notably, the radius of curvature of bladder may be between 2 and 20 feet.

The thigh compression system may also include a pressure monitoring device to provide data which is representative of the pressure of fluid within the bladder. In addition, the thigh compression system may include (1) a first material having hooks, attached to a first portion of the first layer of the flexible material, (2) a second material having loops, attached to a second portion of the first layer of the flexible material, and (3) wherein thigh compression device is secured to a leg of a patient by engaging the first and second materials. The first materials and/or the second material may be laminated to the corresponding flexible material.

In one embodiment, a plurality of the multiple welds (for example, greater than 30) are round and wherein each weld of the plurality of welds is spaced 1 to 2 inches apart. Further, a plurality of the multiple welds restrict expansion of the bladder.

The inflation device, in one embodiment, includes a regulator which controls the pressure of a pressurized air or oxygen source. The regulator may include a diaphragm having at least 1 inch in diameter.

The thigh compression system may also include a quick release connector to provide rapid deflation of the air tight bladder.

Notably, when the thigh compression device is inflated to about 50 mmHg, the venous flow from the leg is reduced and enhancement of veins on peripheral MR angiography is suppressed.

In another principal aspect, the present inventions are directed to a method of reducing venous enhancement on peripheral magnetic resonance angiography. The method includes uniformly compressing the thigh of the patient with a curved compression device that snuggly fits the conical shape of the thigh of an animal (for example, a human) and is inflated without substantially displacing the leg or putting the leg into an unstable position; and thereafter obtaining a first 3D gradient echo MR image. The method further includes injecting a contrast agent into an arm vein of a patient and thereafter obtaining a second 3D gradient echo MR image using the same imaging parameters for obtaining a first 3D gradient echo MR image. The method also includes creating a final image by subtracting the first 3D gradient echo MR image from the second 3D gradient echo MR image.

Again, there are many inventions, and aspects of the inventions, described and illustrated herein. This Summary of the Inventions is not exhaustive of the scope of the present inventions. Moreover, this Summary of the Inventions is not intended to be limiting of the inventions and should not be interpreted in that manner. While certain embodiments have been described and/or outlined in this Summary of the Inventions, it should be understood that the present inventions are not limited to such embodiments, description and/or outline, nor are the claims limited in such a manner. Indeed, many others embodiments, which may be different from and/or similar to, the embodiments presented in this Summary, will be apparent from the description, illustrations and claims, which follow. In addition, although various features, attributes and advantages have been described in this Summary of the Inventions and/or are apparent in light thereof, it should be understood that such features, attributes and advantages are not required whether in one, some or all of the embodiments of the present inventions and, indeed, need not be present in any of the embodiments of the present inventions.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

FIGS. 2A, 2B, 3A and 3B illustrate, in block diagram form, embodiments of systems implementing the thigh compression device according to certain aspects of the present inventions;

DETAILED DESCRIPTION

At the outset, it should be noted that there are many inventions described herein as well as many aspects and embodiments of those inventions.

In a first aspect, the present invention is directed to a thigh compression device and technique to control, time, delay and/or prevent excessive early venous enhancement relative to arterial enhancement and thereby improve and/or enhance MRA images, including peripheral MRA images. In one embodiment, the present invention uses a curved strip of material which is longer on the superior edge and shorter along the inferior edge. When wrapped around the conical or conal shape of the thigh of a subject (for example, a human), the thigh compression device more uniformly conforms to and/or fits around the thigh, providing more even/uniform compression as well as reducing, minimizing and/or eliminating significant movement of the thigh compression device towards the knees of the subject. Notably, a snug fit on the thighs may also enable the thigh compression device to be inflated with less fluid (for example, air) which is faster and less cumbersome for the operator.

The curvature of the thigh compression device confers a conical or cone-like shape which fits the thigh more fully and/or naturally for a more effective compression without the tendency to slide down the leg. It may be useful to make the thigh compression device from material that "grips" the thigh so friction will further reduce, minimize and/or prevent movement of the thigh compression device (for example, sliding to a lose position).

In one embodiment, adjustable straps may allow the degree of angle of the conical or cone-like shape to be adjusted for patients with different size and/or shape legs. In another embodiment, the thigh compression devices may be attached to a pair of shorts or a series of straps like a climbing harness, which enable the devices to be held high on the thigh with little to no risk of the thigh compression devices from sliding down the legs regardless of the shape of the thigh. This combination of blood pressure cuffs, resembling a pair of adjustable shorts, may have straps and/or hook-and-loop fasteners or other easy stick materials that allow it to easily adjust to a wide range of sizes of patients.

Figure 1:
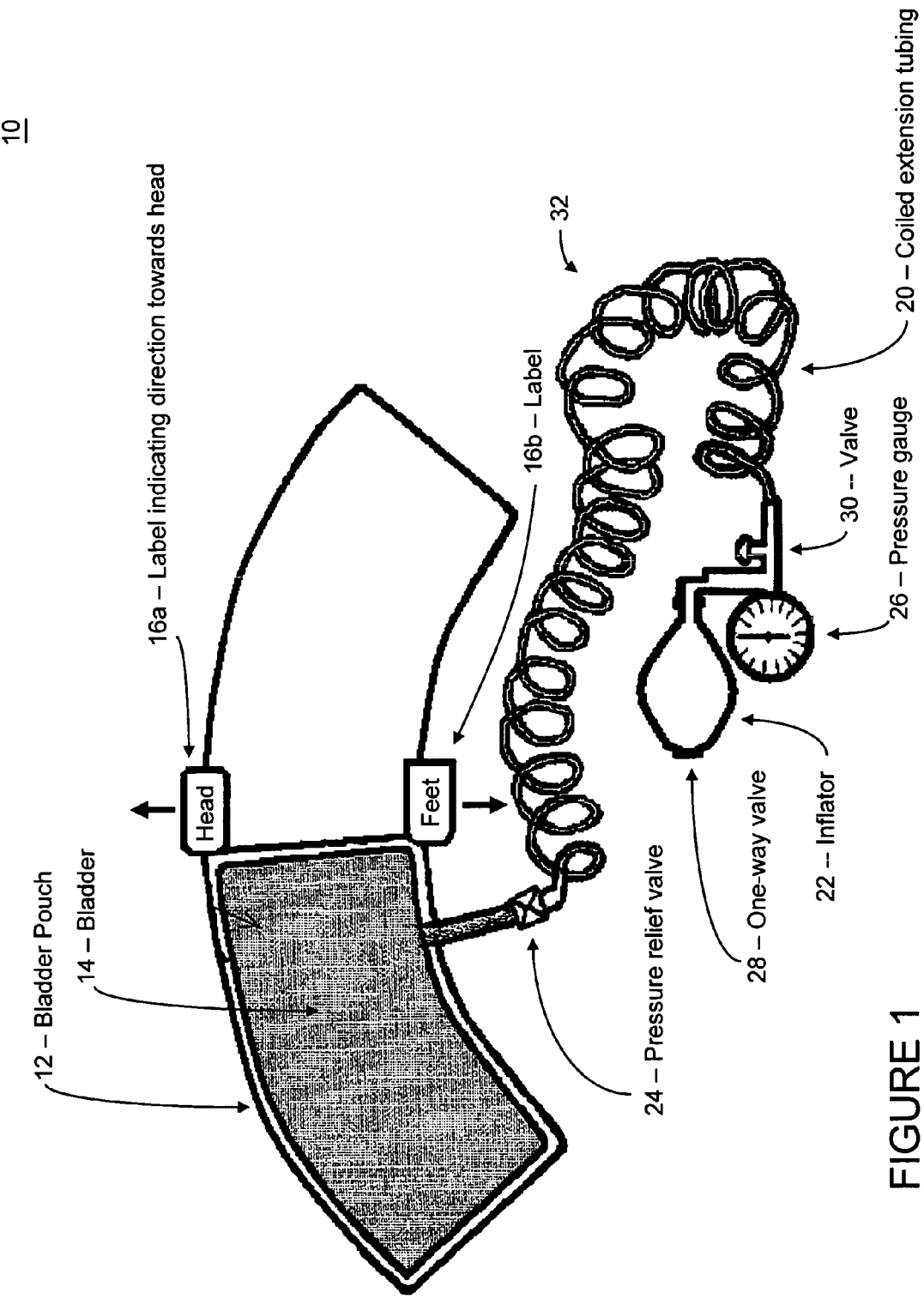
FIG. 1 illustrates an exemplary embodiment of a thigh compression device according to an aspect of the present inventions.

With reference to FIG. 1, in an exemplary embodiment of thigh compression device 10 according to one aspect of the present invention, thigh compression device 10 includes bladder pouch 12 having bladder 14 disposed therein. The labels 16a and 16b identify the "direction" of placement of thigh compression device 10 on the thigh of the patient. The bladder 14 is coupled to extension tubing 20 (which may or may not be coiled) to facilitate inflation by inflator 22. In one embodiment, pressure relief valve 24 may be positioned between bladder 14 and coiled extension tubing 20 to minimize, eliminate and/or reduce over inflation of bladder 14. In addition, pressure relief valve 24 may be employed to quickly or rapidly deflate bladder 14 to facilitate easy removal or repositioning of thigh compression device 10.

In this embodiment, pressure gauge 26 provides the operator with an indication of the pressure of the air in bladder 14. In this exemplary embodiment, thigh compression device 10 also includes one-way valve 28 and valve 30 to allow the operator to quickly release air in bladder 14 and/or reduce the pressure of the air in bladder 14.

With continued reference to FIG. 1, bladder pouch 12 and/or bladder 14 are shaped to adapt to the conical or cone-like configuration or form of the thigh of a human patient. In the exemplary embodiment, bladder pouch 12 and/or bladder 14 of thigh compression device 10 include a radius of curvature of 100 cm, which confers shortening along one edge to reflect the smaller lower portion of the thigh of the human.

Based on experience, a radius of curvature of bladder pouch 12 and/or bladder 14 of about 4 feet (a degree of curvature creating 10% longer superior edge compared to the inferior edge on a 3 foot long thigh, 8 inches wide compression device) may be suitable on the vast majority of people. However, a range in radius of curvature from 2 to 20 feet may also be acceptable.

Notably, it may be advantageous to include more curvature of bladder pouch 12 and/or bladder 14, which tends to cause greater compression along the inferior edge since this may better fix, maintain, control and/or secure the position of thigh compression device 10 thereby minimizing, reducing and/or preventing thigh compression device 10 from "sliding" toward the knees of the human. Moreover, it may be advantageous to have a thigh compression device in which the degree of curvature may be adjusted so as to optimize for individual patients. This may be accomplished by having a band(s) or strap(s) at the inferior and/or superior edge which can be adjusted in length thereby varying the degree of curvature.

In one embodiment, an optimum radius of curvature may be calculated by recognizing that one intention is to have the thigh compression device form a conical section when wrapped around the conically shaped upper thigh. The upper thigh in an average adult will have a circumference that is about 20% greater than the mid-thigh circumference. Where "A" is the circumference of the top of the thigh and "B" is the circumference of the mid-thigh, when un-wrapped, the conical thigh compression device will have a superior edge with a radius of curvature, "R", and length, "A", which is equal to $2\pi R \times \theta/360$, where $\theta$ is expressed in degrees.

Further, the more inferior edge will have a length, "B", which is equal to $2\pi(R-W) \times \theta/360$, where W is the width of the thigh compression device and $\theta$ is expressed in degrees. From these two equations, an enhanced and/or optimum radius of curvature for the superior edge, $R=(W \times A)/(A-B)$. Note that for the standard, straight thigh compression device where the superior edge length, A, is equal to the inferior edge length, B, the calculated radius of curvature will be infinity corresponding to a perfectly straight thigh compression device.

For a typical patient with an upper thigh circumference A=80 cm and a mid-thigh circumference, B=65 cm, and a thigh compression device width, W=15 cm, an enhanced and/or optimum radius of curvature is 80 cm. Because of the range of patient anatomy an enhanced and/or optimum radius of curvature may vary from 40 to 300 cm. For a typical adult whose upper thigh has a circumference of about 24 inches (outside clothing) and a mid-thigh, 8 inches more inferiorly, circumference of about 20 inches, the optimum radius of curvature for the superior edge will be 48 inches. For the inferior edge, an enhanced and/or optimum radius of curvature will be about 8 inches or less (corresponding to the thigh compression device width which is 40 inches).

The length of thigh compression device 10 may be substantially longer than A or B to accommodate for the overlap necessary to secure the thigh compression device 10 with a fastening material, device or system (for example, hook-and-loop fasteners and/or straps/buckles). Typically, the total length is about 100 cm and 15 cm in width, W; however for large patients the length may be longer and for smaller patients the length may be shorter. For example, larger size patients may be 150 cm long with a width of 20 cm, and smaller size patients may be 100 cm long with a width of 15 cm.

The thigh compression device 10 may contain bladder pouch 12 and/or bladder 14 which is short enough to avoid being crimped by these arcs but long enough to provide reasonably uniform compression. This bladder pouch 12 and/or bladder 14 may be about 10 to 20 inches long. Multiple smaller bladders may also be used.

The thigh compression device 10 of this embodiment includes inflator 22, which is implemented using MR compatible materials. The inflator 22 may also include pressure gauge 26, which is also implemented using MR compatible materials. The thigh compression device 10 may employ commercially available MR compatible inflators including for example those available from Heine (Kientalstrasse 7, D-82211, Herrsching, Germany), Welch Allyn (4341 State Street Road, Skaneateles Falls, N.Y.) and/or MDF Instruments, Inc. (26665 Seagull Way, Suite 117 Malibu Calif. 90265). Such inflators have the advantage of being able to both inflate/deflate and monitor pressure with a single tube entering bladder 14. Preferably the inflator should be made entirely of non-magnetic materials to avoid any risk of being affected by the MR scanner magnetic field or interfering with MR images. Since the desired pressure is lower than what is required for normal blood pressure cuffs, the inflation bulb may be larger than normal to facilitate rapid inflation with fewer pumps or squeezes of the bulb. For example a 70 to 150 ml bulb may be suitable instead of the more commonly utilized 50 to 60 ml bulb. For even faster inflation with fewer pumps of greater volume per pump, a cylindrical inflator like a bicycle pump may also be utilized. The pump may be hand or foot operated. Electrical operation of the pump is also possible and may facilitate remote operation so the pump can be activated from another room (e.g. the MRI control room).

The thigh compression device 10 of the present invention may include extension tubing 20 with an innovative design that balances several opposing requirements for enhanced and/or optimal use during the peripheral MRA procedures. This extension tubing 20 is normally compact in length by assuming a coil configuration but can stretch out sufficiently long to allow an operator to stand some distance away outside the MR scanner while inflating or deflating thigh compression devices 20 on the patient inside the MR scanner. The lumen caliber of tubing 20 is sufficient to avoid excessive resistance to air flow for inflation and deflation but has a sufficient wall thickness to avoid kinking. It may also have a cloverleaf or other non-circular luminal profile such that air will continue to flow even in the event of compression or kinking.

In one embodiment, extension tubing 20 includes the spring of rubber (or synthetic rubber, a thermoplastic elastomer or other elastic, non-magnetic material) to return to its coil configuration upon relaxation of the tension. Preferably, the tubing surface is "slippery smooth" to minimize and/or avoid getting caught or clinging to other apparatus and especially to help minimize and/or avoid getting caught in the sliding mechanism of the moving patient table of the MR scanner. The inflating mechanism to which the extension tubing is attached may be placed to the side of the MR scanner table at a sufficient distance from the center of the magnet to maintain a tension in the extension tubing over the full range of patient positions. In this way, the extension tubing is kept away from the sliding table surface to prevent the tubing from getting caught in the sliding table mechanism. In another embodiment, the inflating mechanism can be placed on the patient table adjacent to the patient.

The coiling of extension tubing 20 may have an inner diameter of one quarter inch to 2.5 inches but more preferably is about 0.5 inch. The coil may have an outer diameter of about 1 inch but it may be in the range of 0.5 inch to 3 inches. Note that a large diameter of coil will reduce the pressure drop in the tubing which can be beneficial. This pressure drop will also be reduced when the tubing straightens out from advancing the patient into the MR scanner.

The lumen of extension tubing 20 should be carefully chosen to be sufficient to reduce and/or minimize air resistance but not so large to create a cumbersome tubing with a lot of dead space. Note that due to the law of LaPlace, as the tubing lumen becomes larger in diameter, the force in the tubing increases, requiring ever greater wall thickness to avoid excessive tubing capacitance. This air flow resistance is compounded by the coiling of the tubing which increases resistance to air flow. This will necessitate an inflation pressure in order to get sufficient flow into bladder 14. In one embodiment, the pressure required for laminar flow in a straight tube is equal to 128 times viscosity times tubing length times flow divided by (lumen diameter to the fourth power times π). The pressure may be characterized as:

$$\text{Pressure} = \frac{128 u L Q}{\pi d^4}$$

where: u=viscosity of air
L=length of tubing
Q=flow rate
d=lumen diameter of extension tubing Since the pressure may be a function of the lumen diameter, only a small increase in lumen diameter is required to compensate for the added length. For example, a typical blood pressure cuff tubing has a 2 mm lumen diameter for a 1 meter length of tubing. To increase the length of tubing to 4 meters the lumen only needs to be increased by the fourth root of 4 in order to maintain equal pressure drop. Thus, the lumen will need to be increased by a factor of 1.41 or from 2 to 2.8 mm in order to maintain the same air flow for a given inflation pressure.

Figure 6A:
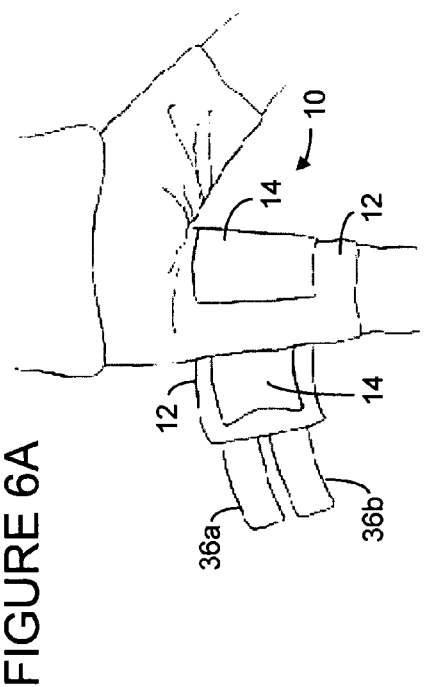
FIGS. 6A-6C illustrate an embodiment of an application of a thigh compression device to a patient, according to an aspect of the present inventions.
Figure 6B:
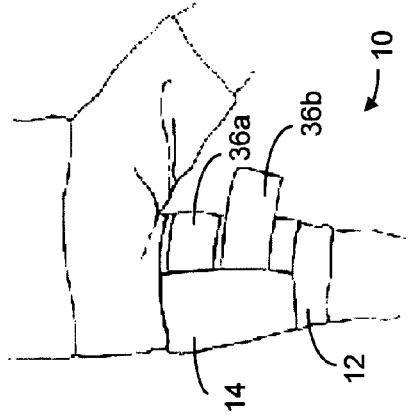
Figure 6C:
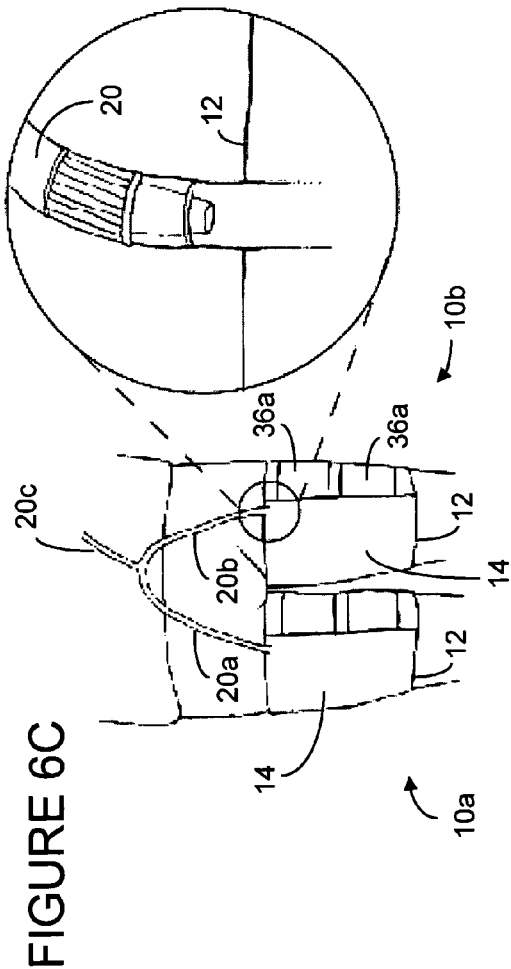

Notably, the coiling of extension tubing 20 also adds resistance which may be minimized by using larger diameter coils. This resistance also diminishes as the coiled tubing stretches out when the patient is inside the magnet. Thus, a lumen diameter of at least 2.5 mm and preferably 3 or 4 mm is useful to minimize resistance to air flow. Also note that it is helpful for all connectors to have a lumen diameter comparable to that of extension tubing 20 so that connectors do not become sites of air resistance and pressure gradients.

Where connectors are used to join tubing 20 (see, for example, FIG. 6C), the connections should be airtight to avoid leakage. In addition, luer locking connectors which are used for intravenous tubing should be avoided so that there will not be any confusion between the extension tubing and IV tubing. Notably, it may be helpful from a patient safety perspective to include a connector for air inflation of the tourniquet that is not easily connectable to the patient's IV line. One suitable connector has a finely threaded screw (finer than the standard luer thread) and an o-ring to seal the connection airtight. Alternatively, the thread could be coarser than the standard luer thread. A press fit type connector mechanism may also be employed. In one preferred embodiment, quick-release connectors are employed. Such quick-release connectors may be disconnected with the press of a button for those connections near the cuffs to facilitate easier placement and removal from the patient as well as more rapid deflation.

Figure 7A:
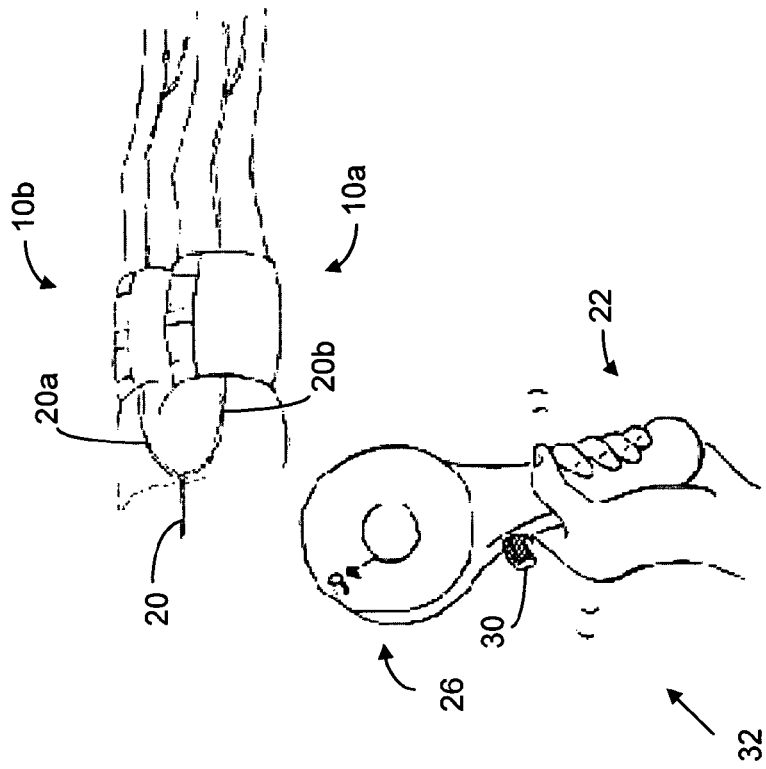
FIGS. 7A and 7B illustrate an exemplary embodiment of the operation of a thigh compression device, according to an aspect of the present inventions.

Notably, thigh compression system 100 of the present invention may include two thigh compression devices 10, one for each thigh of the patient. (See, for example, FIGS. 2A-3B and 6C). The thigh compression system 100 may employ thigh compression devices 10 that have a separate dedicated inflator 22. (See, FIGS. 2A and 2B). Alternatively, in addition to or in lieu of the inflator 22, it may be advantageous to employ an inflation device 32 (a manual hand or foot type inflator or pump type inflator that is coupled to, for example, a pressurized air source) that simultaneously inflates both thigh compression devices 10 via one input from the operator. (See, FIGS. 3A, 3B and 7A). In this way, the pressure applied to each thigh of the patient may be substantially equal and each device 10 simultaneously inflated.

In another embodiment, the bladder of the thigh compression device may be inflated using a pressurized air source with regulator set to the desired pressure. An advantage of this embodiment is that the bladder of thigh compression device may be inflated to a predetermined, desired and/or suitable pressure and maintained at that pressure, even in the event of a leak or minor change in the position of the thigh compression device (relative to the patient), which changes volume of the bladder. For example, the regulator may be set to, for example, 60 mm of mercury, such that there would be continuous maintenance of the pressure of thigh compression device at the correct pressure even if a leak develops and/or has developed in, for example, thigh compression device.

The pressurized air source may be a pressurized air cartridge or it could connect to the pressurized gas source in the wall which is typically available in hospitals and other medical facilities. In this regard, hospitals often have oxygen available at outlets disposed on the wall, typically at a pressure of 50 psi (about 2585 mmHg).

Moreover, pressurized air may also be available in some hospitals. Under this circumstance, a pressure regulator may be employed to adjust the pressure to, for example, 40-60 mmHg, to inflate thigh compression device 10. In one embodiment, the precise pressure may be adjusted by turning a screw that adjusts a spring inside the regulator. In order to make the regulator "non-magnetic", the spring can be made from or of a plastic or inconel, which is a non-magnetic spring metal. A non-magnetic pressure gauge attached to the output of the regulator provides feedback to the operator adjusting the spring to attain the predetermined, desired and/or "correct" pressure as well as to make adjustments in the event, for example, a leak or fluctuation in the pressure source causes the output inflation pressure to change and/or drift. Where oxygen is employed to inflate device 10, it maybe advantageous to thoroughly clean the regulator of any organic lubricants or other combustible material to minimize risk of a fire.

Figure 5:
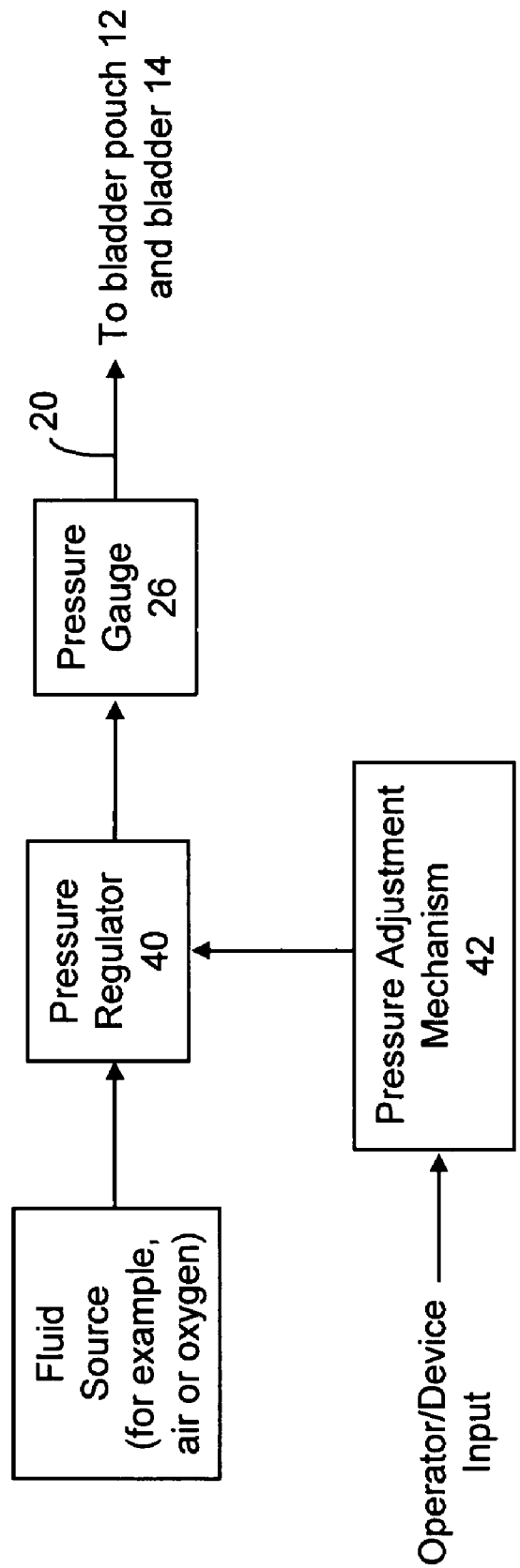
FIG. 5 is a block diagram illustration of an inflation device including a fluid regulating device to control and/or regulate the pressure of the fluid provided by the fluid source, according to an aspect of the present inventions.

Notably, the present inventions may employ any pressure regulator device to control, maintain, and/or ensure a suitable/predetermined inflation of thigh compression device 10. All pressure regulator devices, whether now known or later developed, as intended to fall within the scope of the present inventions. For example, with reference to FIG. 5, pressure regulator device 40 controls, adjusts and/or maintains the output pressure of the fluid (gas or liquid) from the fluid source. A pressure adjustment mechanism 42 allows the operator to control the predetermined, desired and/or suitable pressure of the fluid. The pressure gauge 26 provides the operator with information of the pressure of the fluid at the output of pressure regulator device 40. The output of the pressure gauge 42 is provided to bladder pouch 12 and bladder 14 of thigh compression device 10.

For precise control of the output pressure, it may be useful to use a regulator with a relatively large diaphragm which increases the amount of spring force adjustment for a given pressure change. A suitable device is the Control Air BA700 with modifications to replace the spring with an non-magnetic spring and to replace all other magnetic parts with non-magnetic equivalent parts. For example the steel screws can be replaced with brass screws, the steel diaphragm replaced with an aluminum or plastic diaphragm, the adjustment screw is replaced with a brass or non-magnetic stainless steel adjustment screw and so on.

In another embodiment, thigh compression device 10 may also include a two chamber configuration with an intervening regulator that allows one chamber to be pumped up to a high pressure, higher than 60 mmHg, to serve as a pressure reserve. This high pressure chamber connects to the tubing via a regulator that does not allow more then 60 mmHg to reach bladder 14 of thigh compression device 10. However, in the event that bladder 14 leaks, the high pressure reservoir will serve to continuously replenish the leaking air so that the pressure remains at 60 mmHg.

The undesirable effect of leak may be minimized by having a large air capacitance within the bladder of thigh compression device 10. Multiple compartments with flow restriction may also minimize leak but this may slow inflation and deflation. An electronic inflation system may be employed to monitor the pressure and pump air as needed to maintain the proper pressure.

Notably, pressure relief valve 24 may be incorporated into thigh compression device 10 to prevent excessive inflation. The pressure relief valve 24 may be fixed at a predetermined pressure, for example, 50 or 60 mm of mercury, or can have several positions for different pressures that may be desirable. The pressure relief valve 24 may also have an on/off switch or other mechanism so that an operator may disengage or override relief valve 24 and use thigh compression device 10 at different pressures depending upon the circumstances.

The thigh compression device 10 may enhance uniformity and/or consistency of compression via employing a longer inflation bladder covering more of the thigh circumference or a multi-compartment inflation system. An advantage of the multi-compartment inflation configuration for bladder 14 is that it gives more even compression compared to a single chamber inflation bladder which tends to balloon out in its middle portion. Also a multi-compartment configuration may decompress more slowly in the event of a leak. Positioning of the inflation bladder or multi-compartment mechanism may be along the anterior and lateral aspect of the thigh so as to avoid the underneath and medial aspects which tend to elevate legs or deviate legs laterally upon inflation. This may also avoid inflation directly over subcutaneous bypass grafts which tend to be along the medial thigh.

With continued reference to FIG. 1, bladder 14 of thigh compression device 10 may be, for example, 6, 7 or 8 inches wide which may facilitate effective compression of arteries. However, for compressing the thigh veins which are lower pressure, it may be sufficient for the bladder of thigh compression device 10 to be only 4 inches wide. This also allows more distended vein below the bladder for MR contrast agent dilution and makes it easier to place thigh compression device 10 on the thigh of the patient.

The bladder pouch 12 of thigh compression device 10 may be made from fabric that is strong and resistant to absorbing fluids. In this way, bladder pouch 12 remains relatively clean to enhance its usage lifetime. A suitable material is the Dacron from which sails are made for sail boats. Alternatively, bladder pouch 12 may be made from a soft material such as cotton which is comfortable on the skin of the patient but which can then be disposable or washable, and sterilized.

From a cost perspective, it may be advantageous for only the fabric of the thigh compression device 10 to be disposable. In this way, thigh compression device 10 is designed to allow easy exchange (insertion and removal) of the more expensive bladder 14.

Notably, it may be advantageous to apply a coating to the fabric of bladder pouch 12 in order to make it less likely to absorb fluids that spill onto it. A coating may be applied which is antibacterial in order to minimize the chance that bacteria picked up from one patient could get transferred to the next patient.

The bladder pouch 12 and/or bladder 14 of thigh compression device 10 is longer than the typical circumference of the leg so that there will be overlap of at least 4 to 6 inches of thigh compression device 10 to facilitate affixing bladder pouch 12 (and pouch 14) into the conical-like shape. The thigh compression device 10 may be affixed to the leg using any technique, whether now known or later developed. For example, thigh compression device 10 may employ a hook-and-loop fasteners to secure bladder pouch 12 in the conical-like configuration around the leg. With typical hook-and-loop fasteners it may be advantageous to include about 10 square inches (or more) of overlap to ensure that the fasteners will grip sufficiently to prevent bladder pouch 12 from popping open during inflation of bladder 14.

Notably, thigh compression device 10 may be affixed to the thigh using buckles, snaps, straps or other mechanism, provided that thigh compression device 10 does not use a material that interferes with the MR imaging and/or MR scanner. Preferably metal should be avoided. Even metal that is non-magnetic and in theory does not interfere with the image may be confusing for technologists operating the scanner who cannot readily tell that it is an acceptable metal by its appearance. Virtually all plastics are acceptable and plastics are easily recognized as acceptable for use in MR scanners.

In one exemplary embodiment, two thigh compression devices 10 were manufactured—one for each leg. Each thigh compression device 10 was substantially identical and included a radius of curvature of the superior edge of 44 inches and a width of 8 inches. (See, for example, FIG. 2A). The bladder 14 was manufactured from a polyurethane material and was sewn into the bladder pouch 12 to allow positioning of inflation bladder 12 along the anterior-lateral portion of the thigh. A coiled extension tubing 20, having a diameter of 1 inch, was manufactured from a latex-free material. The coiled extension tubing 20 was capable of being "stretched" to an uncoiled length of about 8 feet. Notably, the inflation bladder tubing added two feet to the total tubing length (i.e., about 10 feet in total).

Moreover, because most peripheral MRA is performed with the patient entering the MR scanner feet first, the inflation bladder of the thigh compression devices 10 was oriented with the inflation tubing exiting the bladder pouch via the longer edge which is towards the head and towards the opening of the MR scanner. The inflation bladder tubing attached to inflator 22, which may be a G5 Heine type inflator.

Notably, thigh compression devices 10 may be generic to the thigh (see, for example, FIG. 2A) or tailored to a left and right thigh (thigh compression devices 10L and thigh compression devices 10R, respectively (see, for example, FIG. 2B)). The thigh compression devices 10L and thigh compression devices 10R may provide a more conformal fit to the conical or cone-like shape of the respective thigh, in order to limit, reduce and/or eliminate detrimental movement of the device 10.

In another exemplary embodiment, thigh compression device 10 is made from two layers of a material (for example, an elastic material such as polyurethane) which is sealed together with RF welding. In order to avoid the device "ballooning" during inflation, it can be spot welded about every 1 to 2 inches with RF welding such that the compression device has a limited volume of expansion and retains its flat shape during inflation. An attachment mechanism may be included to secure the thigh compression device to the patient (for example, a surface suitable for hook-and-loop fasteners (for example, fuzzy) which is laminated to one side of this welded bilayer so that hook-and-loop fastener straps can be used to secure it tight around the thigh). For example, where hook-and-loop fastener straps are employed, a spacer of elastic material may be included in order to allow easy adjustment to a range of positions. This composite bilayer has a relatively stiff configuration which allows for easy positioning on the thigh.

Figure 4A:
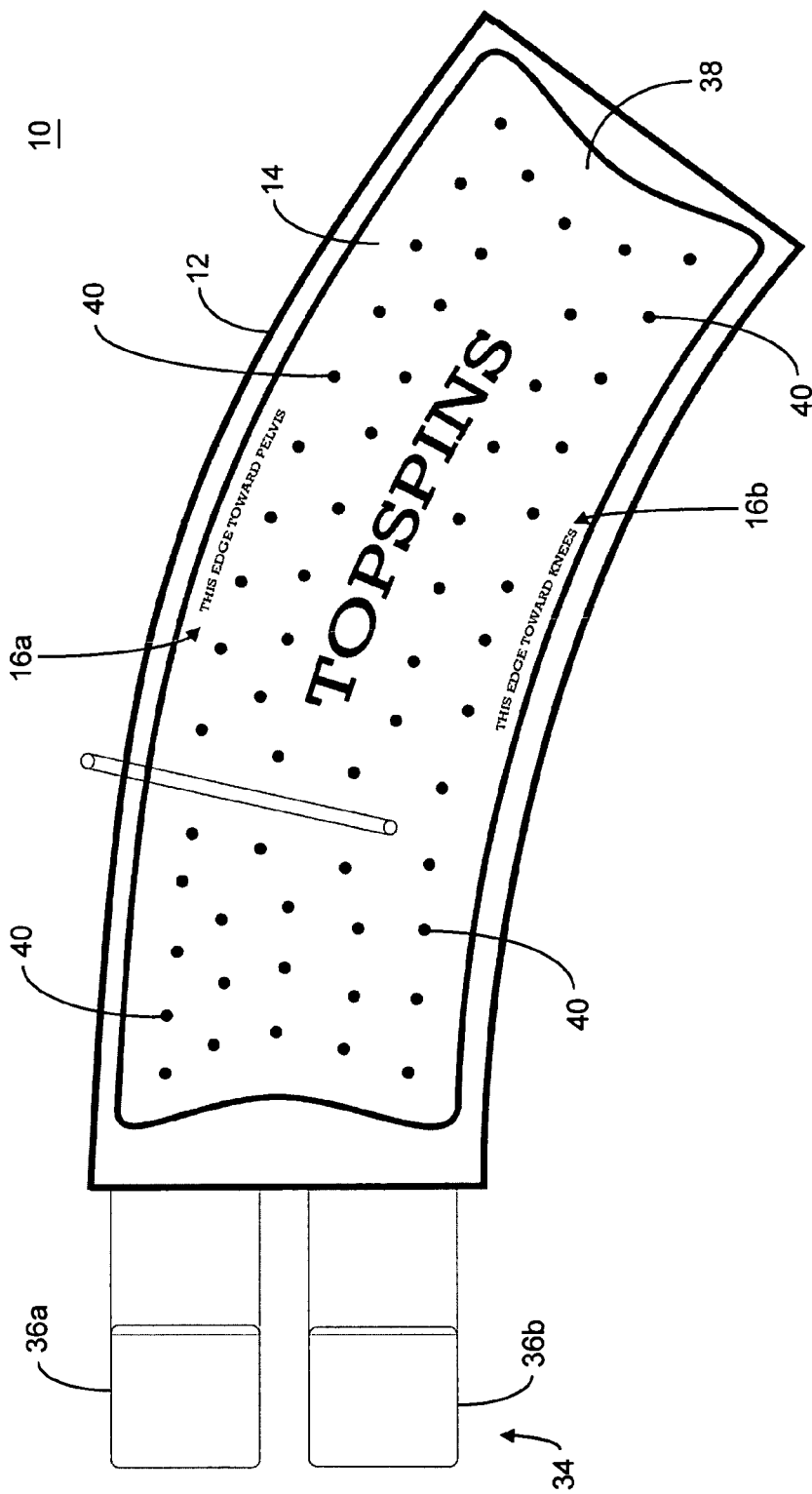
FIGS. 4A and 4B illustrate other exemplary embodiments of various aspects of a thigh compression device according to an aspect of the present inventions.
Figure 4B:
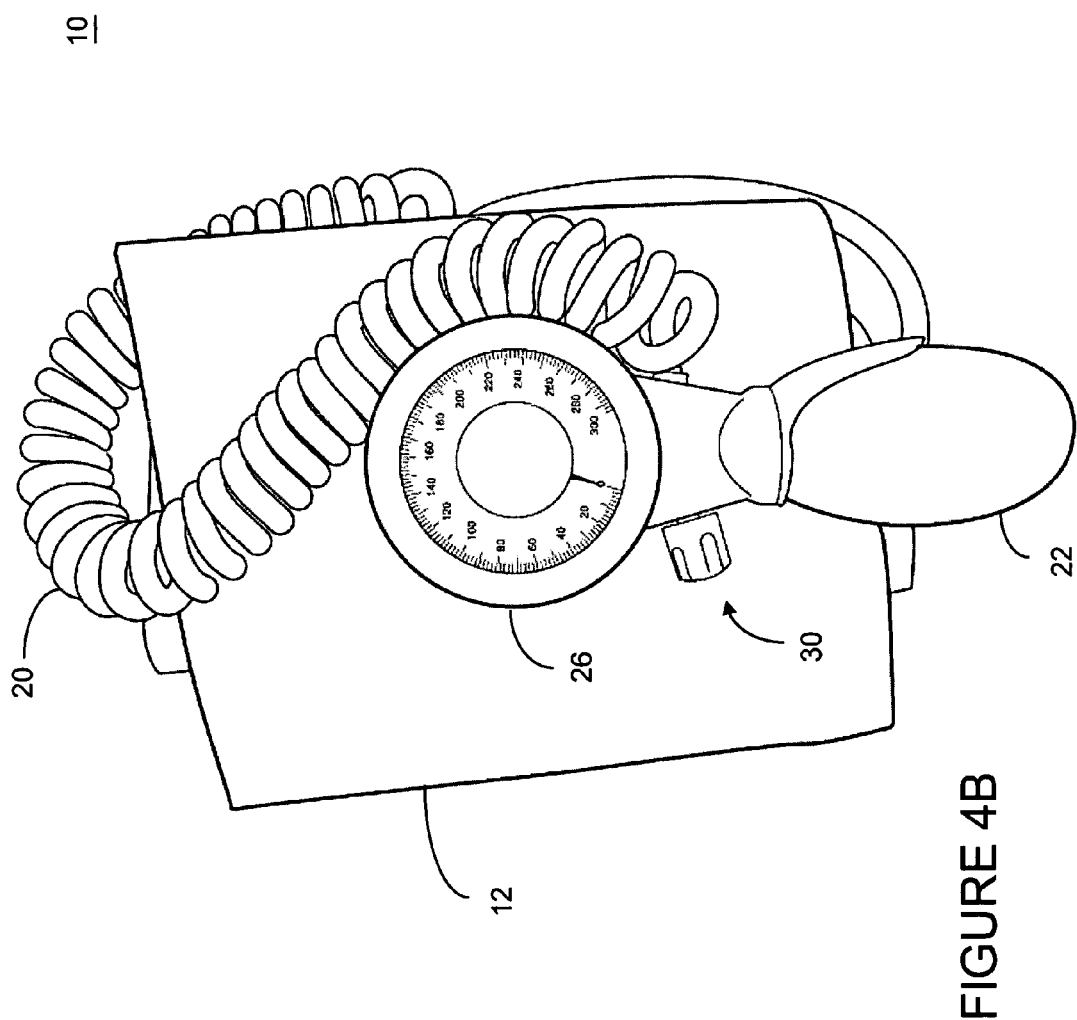

In particular, with reference to FIGS. 4A and 4B, in one embodiment, thigh compression device 10 may be fabricated by sealing two pieces of flexible curved material together using RF welding or other sealing methods to form a curved bladder pouch 12 having an integrated inflatable bladder 14.

When inflated with a fluid (i.e., a gas (for example, air) or a liquid (for example, water)), bladder pouch 12 and bladder 14 apply pressure to the leg of the patient. On predetermined areas of an outer surface of the tourniquet, attachment mechanism 34 is disposed in order to secure thigh compression device 10 to the patient.

In one example, bladder pouch 12 and bladder 14 may be formed from a 0.012 inch thick urethane inner layer (layer that contacts the patient, for example, the skin of the patient or the pants that the patient is wearing) and a laminate of 0.012 inch thick urethane and tricot (hooks fasteners). The thigh compression device 10 may also include an ⅛ inch thick foam in the laminated layer. In one embodiment, bladder pouch 12 and bladder 14 includes a longer curved edge with a radius of curvature of 4 feet (the edge towards the pelvis) and a shorter curved edge with a radius of 32 inches (the edge towards the knee). In this exemplary embodiment, bladder pouch 12 is about 8 inches wide. During RF welding of the inner layer of urethane to the laminate, a 3/16 inch seal is created at the outer edge.

Notably, it may be useful to provide a double seal around the outer margin of the curved bladder pouch 12 in order to minimize, reduce or limit the possibility of fluid leaking from thigh compression device 10 which may enhance the durability and/or lifetime thereof. In this regard, with reference to the exemplary embodiment above, a secondary seal of 3/16 inch may be formed approximately ½ inch in from the outer edge.

The seal created during RF welding should be airtight and ideally should withstand a pressure of at least 200 to 300 mmHg. An inflation tube made of ¼ inch, inner diameter (ID), ⅜ inch outer diameter (OD) is welded into place ⅓ of the length in from left edge (where elastic is sewn) and/or along the edge where elastic is sewn.

In one embodiment, attachment mechanism 34 may be one or more straps (for example, straps 36a and 36b) including hooks or loops (for example, tricot) that are located on predetermined portions of the outer surface of one end or side of bladder pouch 12 (i.e., on the laminate of 0.012 inch thick urethane that does not directly contact the patient) and a corresponding piece of loops or hooks fabric 38 are located on the other end or side of the outer surface of bladder pouch 12. In this way, the hooks or loops on the one side or end of thigh compression device 10 may engage the loops or hooks fabric on the other side or end of thigh compression device 10 in order to facilitate secure thigh compression device 10 around the leg of the patient. One source of loops or hooks fabric is identified by the "Velcro" brand. For example, two elastic straps 36a and 36b, each 3 inch by 3 inch, attached by sewing, located on left margin (approximately 1 inch) may be attached by sewing to two pieces of 3 inch by 3 inch hooks fasteners, cut to round the corners. This "extra" elastic piece provides greater adjustability in the positioning of the (hook-and-loop fasteners) adhesion mechanism.

Notably, on the tricot surface a logo may be applied (for example, www.TOPSPINS.com) to the middle by hotstamp. In addition, directional labels indicating "this edge toward pelvis" and "this edge toward knees" are hot stamped onto the superior (long) and inferior (short) edges, respectively, to facilitate application or operation of thigh compression device 10.

In one embodiment, bladder pouch 12 and bladder 14 include a plurality of chambers (for example, formed by a plurality of weld or spot seals 44). In this embodiment, the volume of fluid (gas or liquid) that is necessary to inflate thigh compression device 10 to a suitable pressure (for example, approximately 60 mm Hg for subsystolic inflation or approximately 200 mm Hg for supra-systolic inflation) may be reduced. For example, fifty-nine ¼ inch spot welds are distributed evenly over the surface of thigh compression device 10, with the exception of a 2-3 inch swath in the center where there are no spot welds. In this example, the inflation volume for a thigh compression device 10 without spot seals was double that required for a thigh compression device 10 with a plurality of spot seals (sometimes referred to as RF spot welds) 44, for example, fifty-nine spot seals.

Figure 7B:
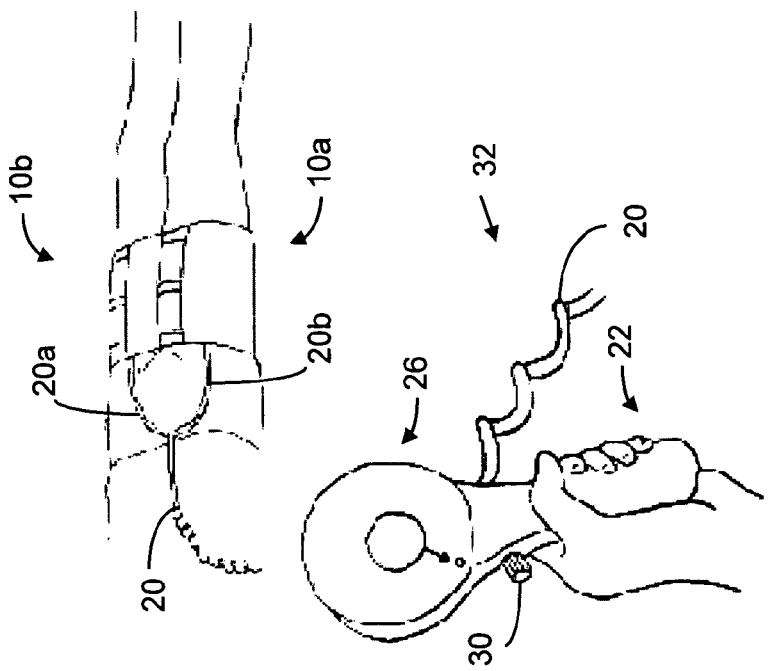
Figure 8A:
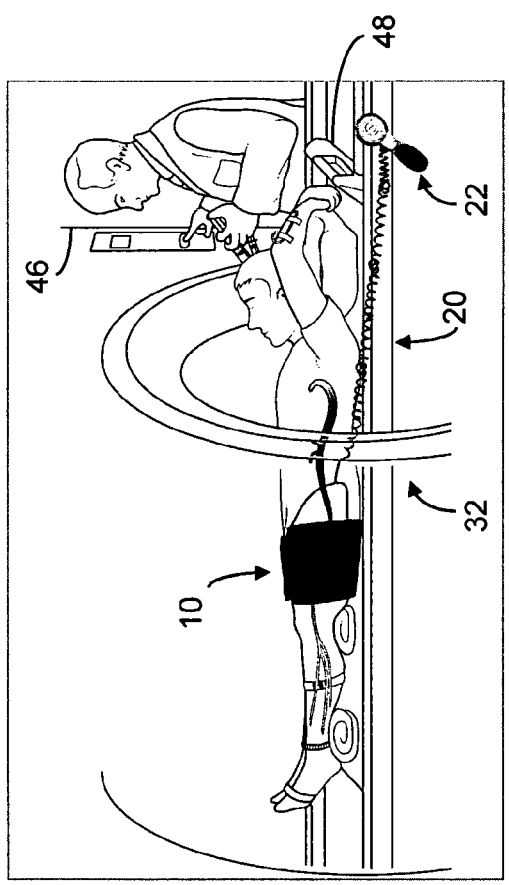
FIGS. 8A and 8B illustrate an exemplary embodiment of the operation of a thigh compression device in conjunction with an MR scanner, according to an aspect of the present inventions.
Figure 8B:
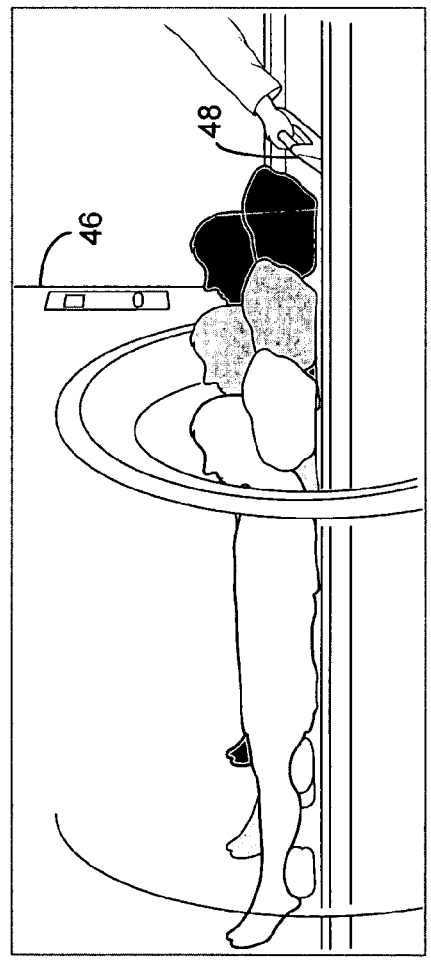
Figure 9C:
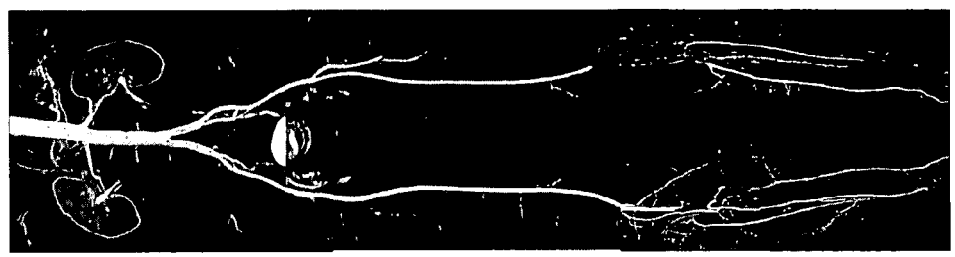
FIG. 9C illustrates an exemplary image of the peripheral vasculature that was obtained using the images and/or data of FIGS. 9A and 9B (i.e., a subtraction image)
Figure 9B:
FIG. 9B illustrates an exemplary contrast agent enhanced image of the peripheral vasculature wherein the image data was acquired using a thigh compression device according to an aspect of the present inventions.
Figure 9A:
FIG. 9A illustrates an exemplary pre-contrast agent "mask" image of the peripheral vasculature.

In operation, thigh compression devices 10 are placed on the legs of a patient undergoing contrast agent enhanced peripheral magnetic resonance angiography (MRA) and noted to fit snug with no tendency to slip towards the knees during and/or after inflation of the bladder. (See, for example, FIGS. 4A, 6A, 6B and 6C). In one embodiment, bladders 14 of the thigh compression devices 10 may be inflated immediately prior to acquisition of the pre-contrast agent mask and the inflation pressure may be periodically checked to ensure there was no air leak. (See, for example, FIGS. 7A and 7B). The subject may then be placed into MR scanner 46 by advancing MR patient table 48 into MR scanner 46. (See, for example, FIG. 8A. Thereafter, pre-contrast agent mask data collection and contrast agent enhanced data collection sequences may be performed. (See, for example, FIG. 8B). The pre-contrast agent mask "run" (FIG. 9B) and arterial phase contrast agent enhanced "run" (FIG. 9A) were obtained and subtracted (see, FIG. 9C). The contrast agent enhanced peripheral MRA may be performed using well known techniques. Indeed, any technique for performing contrast agent enhanced peripheral MRA whether now known or later developed are intended to fall within the scope of the present invention.

Notably, as mentioned above, it may be advantageous to position bladder pouch 12 and/or bladder 14 of thigh compression devices 10 on the thigh as "high" as possible (as described above, close to the groin area of the patient), due to a large extent on the cone-like shape of thigh, which is larger near the groin area of the patient and smaller near the knee area (reaching a minimum diameter around the knee). (See, for example, FIGS. 6B and 7B). Although effective compression may be obtained using an elastic tourniquet, it may be more reliable, reproducible and effective if the compression is applied with the bladder and bladder pouch configuration, as described above, that can be inflated to a precise pressure. In addition, compression of the deep veins is more effective when the width of the bladder and bladder pouch is similar to or greater than the diameter of the leg of the patient. Notably, thigh compression devices 10, which is approximately 6 inches wide, and can be inflated to 50 or 60 mm Hg, to provide suitable, maximum and/or effective venous compression.

In a first exemplary operational embodiment, thigh compression device(s) 10 was wrapped around the upper portion of one or both thighs of the test subject and secured with hooks fasteners. (See, for example, FIGS. 6A, 6B and 6C). The test subjects were then positioned on a MR scanner/patient table of a 1.5 Tesla MR scanner. (See, for example, FIGS. 8A and 8B). In two of the five volunteers, a (four) channel phased array coil was positioned over the calves for signal reception in that region. The body coil was used for signal transmission for abdomen pelvis thighs calf and for signal reception at the abdomen pelvis and thighs. In three patients, the signal reception at the calf and feet was performed with a birdcage coil array. The patients were imaged with coronal 3D spoiled gradient echo pulse sequence covering three stations (abdomen-pelvis, thigh, calf) in three subjects and four stations (abdomen-pelvis, thigh, calf and feet) in two subjects. Data acquisition times for the abdomen-pelvis and thighs were 20 seconds and 16 seconds, respectively, with 5 seconds for table re-positioning in between stations.

For the calf the image acquisition time was 60-70 seconds depending upon the number of slices required. When both calf and feet were imaged for the four station protocol, the feet were imaged first with a scan time of 33 seconds and the calf was imaged last. This sequence was used because venous contamination shows up first in the feet.

Prior to the pre-contrast agent mask acquisition, thigh compression device 10 was inflated to 60 mm Hg with a conventional inflator having a non-magnetic pressure gauge. Then the pre-contrast agent mask acquisition was performed followed by the 3D Gd:MRA sequences during bolus injection of 40 to 50 ml (depending upon subject weight) gadopentetate dimeglumine at about 2 ml/second. (See, for example, FIGS. 8A, 9A and 9B). Following data acquisition, the final station was repeated until venous enhancement occurred.

In all five subjects, arterial phase MRA was obtained for the entire lower extremity with no venous contamination. Venous in the calf arrival time averaged 4:33 minutes for these subjects who all had normal appearing arteries.

Notably, the embodiment illustrated in FIGS. 4A and 4B may be employed or implemented in conjunction with the embodiments of FIGS. 2A, 2B, 3A and 3B.

In a second exemplary embodiment, a 3D bolus chase peripheral MRA was performed with approximately 45 ml Gadolinium injected at 1.5 ml/s for 25 patients with peripheral vascular disease. Notably, indications for the examination included: claudication (n=19), cellulitis (n=1), ulceration (n=1) and post-operative surveillance (n=4). There were 15 males and 10 females ranging in age from 24 to 84 (mean age=66 years). A total of 49 legs were analyzed due to one amputation. For each patient, the third station (calf station) of the bolus chase examination was repeated until venous enhancement was observed. In this way the time to venous enhancement was measured. In all patients, thigh compression device 10 was employed (for example, thigh compression device illustrated in FIG. 4A). In this exemplary embodiment, thigh compression device 10 was inflated to 60 mmHg just prior to the pre-contrast agent mask acquisition and maintained inflated until venous enhancement.

Venous enhancement on the first phase of calf imaging was observed in only six legs (12%) and it was mild and mostly superficial. The remaining 43 legs had no venous contamination on the first calf station. In 15 out of 49 legs, venous enhancement (with the tourniquet inflated to 60 mm Hg) did not occur even after repeating the calf station three times. For these legs, venous enhancement was assumed to occur on the next repetition. With this conservative assumption, the mean time to venous enhancement in the calf was 134±40 seconds. This compares to 67 seconds to venous enhancement in the calf reported in the literature for patients without thigh compression.

Suppression of venous signal during the dynamic phase of contrast injection may also be useful with computed tomographic angiography or other imaging techniques that involve contrast agent enhanced imaging of arteries. In addition to suppressing visualization of veins during the dynamic phase of contrast enhancement, the tourniquets may be used in a different fashion to enhance visualization of veins. For example, the contrast agent (for example, gadolinium) may be allowed to reach equilibration between arteries and veins which generally happens in a few minutes. Then when the thigh compression device 10 are inflated, the veins will gradually dilate and be easier to image due to their larger size.

Although both arteries and veins enhance, generally the large, dilated veins are easier to see compared to the arteries which are much smaller.

It is also possible to obtain an image where veins enhance but not arteries. This can be done by inflating the cuff on the thigh and rapidly filling the vein by injection of contrast into a vein peripheral to the cuff (for example, in the dorsal vein of the ipsilateral foot). When using gadolinium, it may be necessary to dilute the gadolinium (for example, 1 part gadolinium to 20 parts normal saline) in order to avoid excessively concentrated gadolinium with a T2* that is too short to image.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the embodiments, features, attributes and advantages of the inventions described and illustrated herein are not exhaustive, and it should be understood that such other, similar, as well as different, embodiments, features, attributes and advantages of the present inventions are within the scope of the present inventions.

Figure 10:
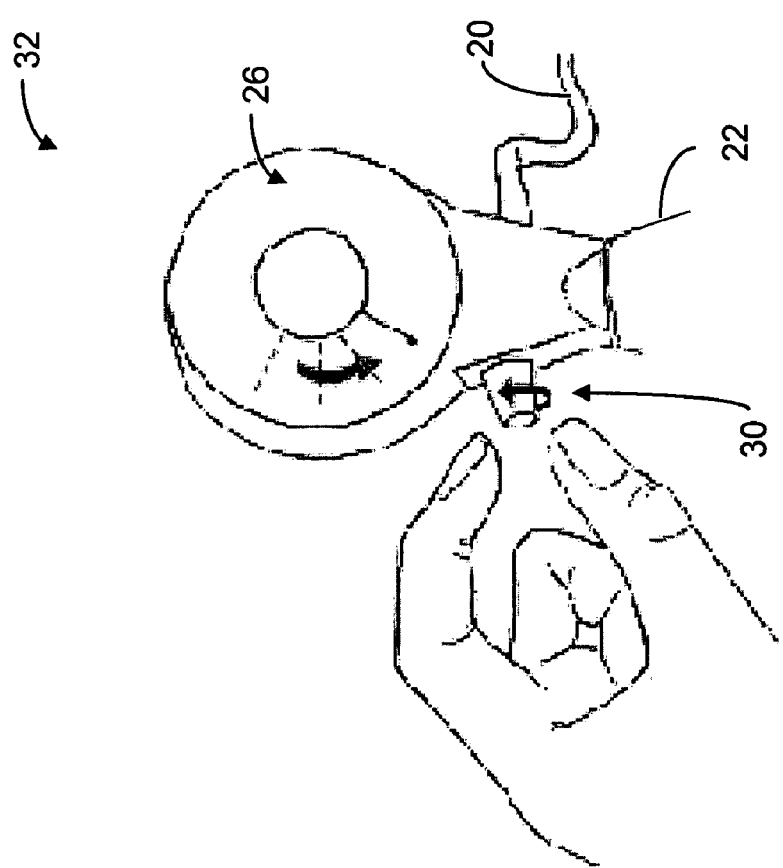
FIG. 10 illustrates an exemplary embodiment of a portion of the inflation device of the thigh compression device of FIGS. 4A and 4B, according to an aspect of the present inventions.

For example, as mentioned above, pressure relief valve 24 may be positioned between bladder 14 and coiled extension tubing 20. (See, FIG. 1). The pressure relief value may also be located to facilitate quick or rapid deflation of bladder 14 to, for example, permit easy removal or repositioning of thigh compression device 10. A valve 30 may be located near the inflator 32 as well (See, for example, FIG. 10). In this way, the operator may quickly release air in bladder 14 and/or reduce the pressure of the air in bladder 14 without contacting the patient, bladder pouch 12 and/or bladder 14—all of which may be less accessible when the patient is in MR scanner 46. (See, for example, FIGS. 8A and 8B).

Figure 11:
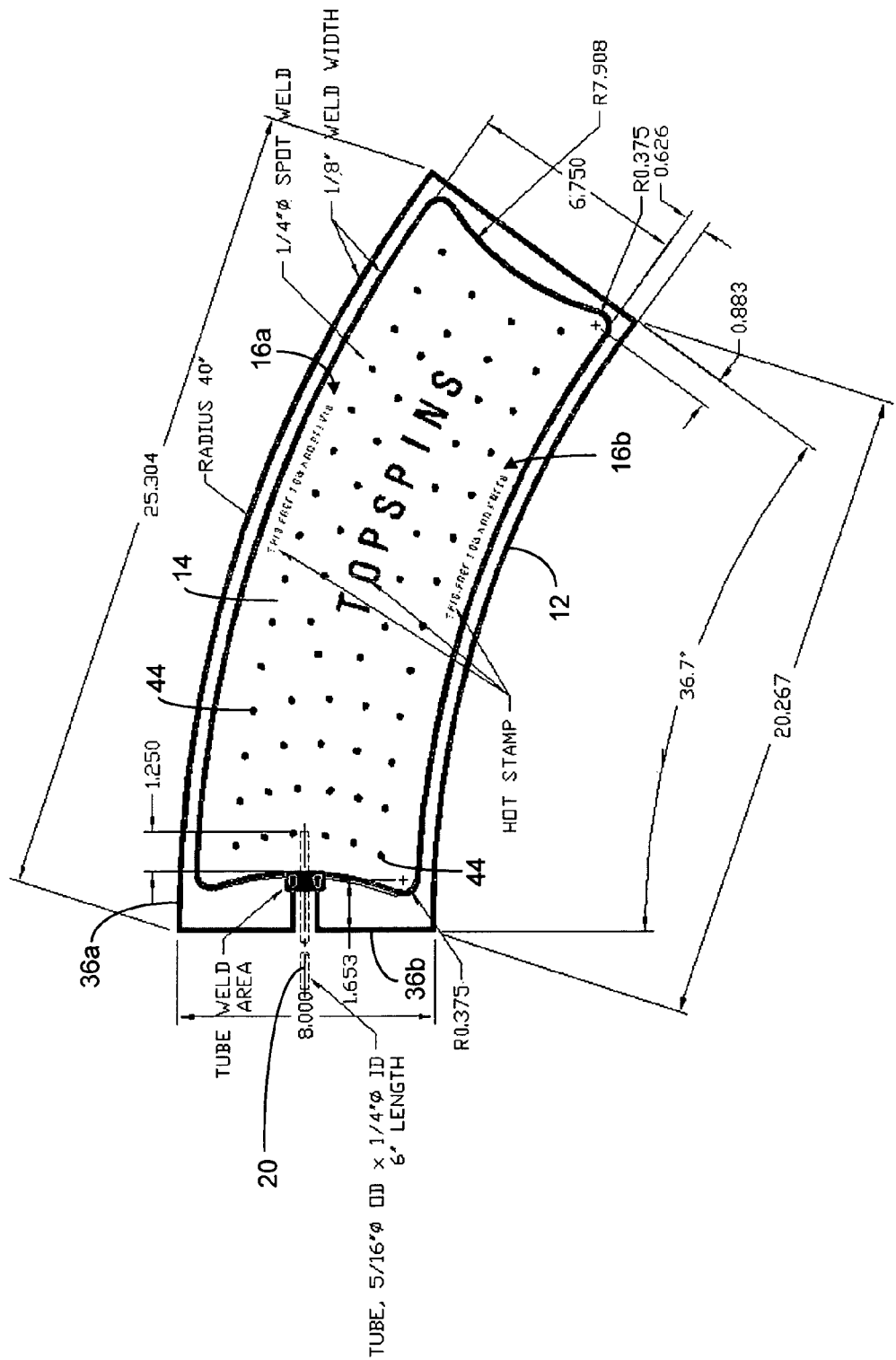
FIG. 11 illustrates another exemplary embodiment of a thigh compression device according to an aspect of the present inventions.
Figure 12:
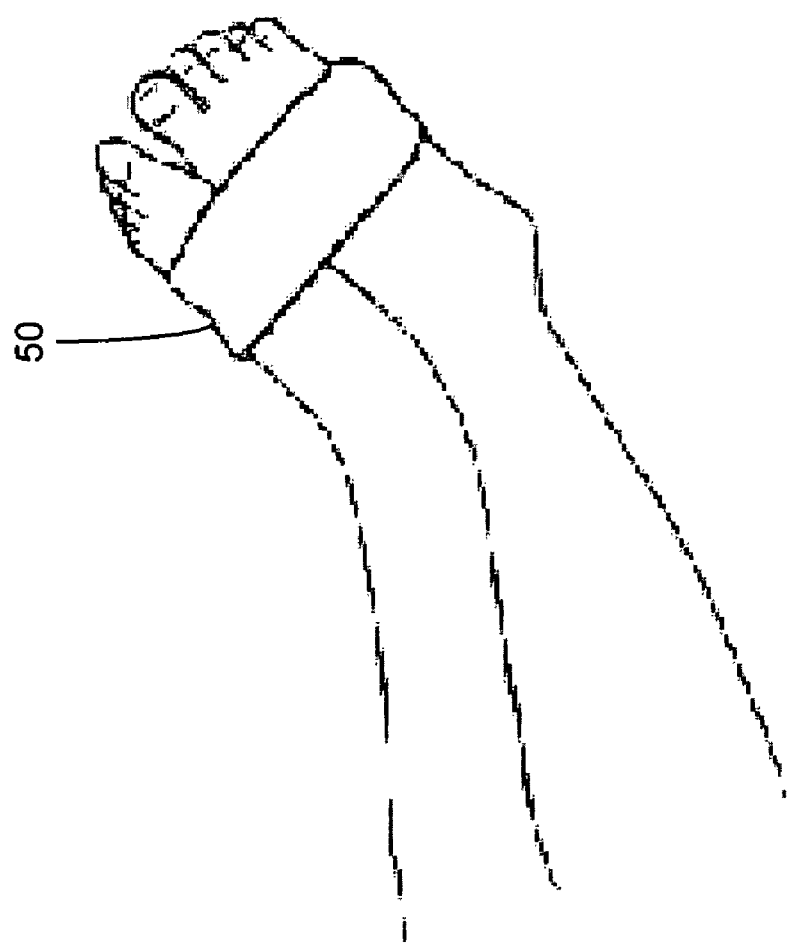
FIG. 12 illustrates an exemplary embodiment of a foot stabilizing mechanism which may be used in conjunction with any embodiment of the thigh compression devices of the present inventions.

Further, although inflation tubing 20 (which may or may not be coiled) has been described and illustrated as attaching/connecting to the longer edge of thigh compression device 10, such tubing 20 may attach/connect to thigh compression device 10 along the shorter edge. This may be advantageous when the patient is oriented head first into the MR scanner. Such a configuration may be more convenient to employ thigh compression device 10 during performance of whole body MRA which is typical performed with head first positioning. In yet another alternative, inflation tubing 20 may exit along the end (narrower dimension) of thigh compression device 10 so that tubing 20 may be more easily directed toward the head or feet allowing the patient to be positioned either head first or feet first into the magnet. (See, for example, FIG. 11).

As shown in FIGS. 1, 4A, 6C, 7A, 7B, 8A, and 11, the bladder has exactly one port to receive and expel inflation air.

Moreover, it may be advantageous to employ foot stabilizing mechanism 50 to facilitate the patient's ability to restrain or control the movement of the feet. In this embodiment, the foot stabilizing mechanism 50 is a band or strap that secures the feet together, which may make it relatively easier to eliminate, minimize and/or prevent foot movement as well as leg movement. Straps over the legs for additional immobilization may also be helpful. The foot stabilizing mechanism 50 and straps may be employed with any of the embodiments of thigh compression device 10 and/or thigh compression system 100 described and illustrated herein.

In addition, as mentioned above, the thigh compression device may be inflated using any form of pressurized source (for example, hand action with respect to a hand-inflator). The devices may be inflated using an oxygen or pressurized air source, as are commonly available in MR scanner rooms. In this embodiment, the thigh compression device may be inflated using a high precision, high flow, low pressure regulator (for example, to about 50 mm Hg). Indeed, a two stage pressure regulator may be employed if inflating with a portable oxygen tank which has higher pressures than the piped air coming from outlets mounted in the wall.

Further, the thigh compression device, in one embodiment, may include a urethane laminate with a hook-and-loop fastener surface and a curved shape optimized for a snug fit on the conical shape of the leg. In addition, uniformity of the inflation of the bladder may be enhanced and controlled via the spot welds (for example, 59) which may also prevent excessive bulging in any one area and minimize the volume of air required for inflation. Indeed, this embodiment may also minimize any shift in the legs that occurs as a result of inflating the cuffs.

A double seal may be employed to minimize leaking. In this regard, the thigh compression device includes o-ring sealed connectors to a coiled conduit for inflation via an MRI compatible hand-inflator or via an auto-inflator connected to a pressure source.

The above embodiments of the present invention are merely exemplary embodiments. They are not intended to be exhaustive or to limit the inventions to the precise forms, techniques, materials and/or configurations disclosed. Many modifications and variations are possible in light of the above teaching. It is to be understood that other embodiments may be utilized and operational changes may be made without departing from the scope of the present invention. As such, the foregoing description of the exemplary embodiments of the invention has been presented for the purposes of illustration and description. It is intended that the scope of the invention not be limited to the description above.

What is claimed is:

1. A thigh compression device for use with magnetic resonance imaging equipment, the thigh compression device comprising:
  a bladder pouch having two opposed faces, the faces each shaped as an angular sector of an annulus and joined to one another along four edges, the first edge being an outer arcuate edge of the sector, the second edge being an inner arcuate edge of the sector, and the third and fourth edges being radial edges of the sector, wherein the first edge is longer than the second edge;
  an inflatable, double-sealed bladder, adapted to be inflated by air, disposed within the bladder pouch, and comprising multiple round internal welds spaced 1 to 2 inches apart that attach opposed sides of the bladder to one another and that restrict how much the bladder can expand when inflated, the bladder including exactly one port to receive and expel inflation air;
  extension tubing coupled to the port and passing through the bladder pouch on the first edge; and
  an attachment mechanism adapted to secure the bladder pouch and the inflatable bladder to a thigh of a human, wherein when the thigh compression device is affixed on the thigh of the human using the attachment mechanism, the bladder pouch and the inflatable bladder form a conical frustum so as to conform to the conical shape of the thigh.

2. The thigh compression device of claim 1 wherein the length of the first edge of the bladder pouch is greater than about 20 inches and less than about 50 inches.

3. The thigh compression device of claim 1 wherein the length of the third and fourth edges of the bladder pouch is greater than about 4 inches and less than about 12 inches.

4. The thigh compression device of claim 1 wherein the first edge of the bladder pouch has a radius of curvature between 2 and 20 feet.

5. The thigh compression device of claim 1 wherein the inflatable bladder is inflatable with a gas or liquid to a pressure of greater than about 40 mm Hg.

6. The thigh compression device of claim 5 further including an inflation device, coupled to the extension tubing, to inflate the inflatable bladder.

7. The thigh compression device of claim 1 further including a pressure gauge, coupled to the extension tubing or inflatable bladder, to provide information which is representative of the pressure of the air in the inflatable bladder.

8. A thigh compression system for use with magnetic resonance imaging equipment, the thigh compression system comprising first and second thigh compression devices, each according to claim 1, wherein:
   in the first thigh compression device, the attachment mechanism is adapted to secure the bladder pouch and the inflatable bladder to a left thigh of a human;
   in the second thigh compression device, the attachment mechanism is adapted to secure the bladder pouch and the inflatable bladder to a right thigh of a human; and
   the system further comprises an inflation device, coupled to the extension tubing of the first and second thigh compression devices, to simultaneously inflate the inflatable bladder of each of the first and second thigh compression devices.

9. The thigh compression system of claim 8 wherein the length of the first edge of the bladder pouch of each of the first and second thigh compression devices is greater than about 20 inches and less than about 50 inches.

10. The thigh compression system of claim 8 wherein the length of the third and fourth edges of each bladder pouch is greater than about 4 inches and less than about 12 inches.

11. The thigh compression system of claim 8 wherein the first edge of each bladder pouch of each of the first and second thigh compression devices has a radius of curvature between 2 and 20 feet.

12. The thigh compression system of claim 8 wherein the inflatable bladder of each of the first and second thigh compression devices is inflatable with air to a pressure of greater than about 40 mm Hg.

13. The thigh compression system of claim 8 further including a pressure gauge, coupled to the inflation device, to provide information which is representative of the pressure of the air in the inflatable bladder of each of the first and second thigh compression devices.

14. A thigh compression system for use with magnetic resonance imaging equipment, the thigh compression system comprising:
   a thigh compression device including:
      first and second layers of flexible material welded together to form an air tight bladder
         wherein the bladder has two opposed faces, the faces each shaped as an angular sector of an annulus and joined to one another by double seals along four edges, the first edge being an outer arcuate edge of the sector, the second edge being an inner arcuate edge of the sector, and the third and fourth edges being radial edges of the sector, wherein the first edge is longer than the second edge,
         and wherein the bladder is inflatable by air and has exactly one port to receive and expel inflation air, the port being located along the first edge of the bladder; and
         multiple round welds spaced 1 to 2 inches apart within the bladder that attach opposed sides of the bladder to one another and that restrict the amount that the bladder expands when inflated;
      extension tubing coupled to the bladder; and
      an inflation device, coupled to the extension tubing of the thigh compression device, to inflate the inflatable bladder.

15. The thigh compression system of claim 14 wherein the length of the first edge of the thigh compression device is greater than about 20 inches and less than about 50 inches.

16. The thigh compression system of claim 14 wherein the radius of curvature of the first edge is between 2 and 20 feet.

17. The thigh compression system of claim 14 further including a pressure monitoring device to provide data which is representative of the pressure of air within the bladder.

18. The thigh compression system of claim 14 further including:
   a first material having hooks, attached to a first portion of the first layer of the flexible material;
   a second material having loops, attached to a second portion of the first layer of the flexible material; and
   wherein thigh compression device is secured to a leg of a patient by engaging the first and second materials.

19. The thigh compression system of claim 18 wherein the first material or the second material is laminated to the corresponding portion of the first layer of the flexible material.

20. The thigh compression system of claim 14 wherein the plurality of the multiple welds is greater than 30 welds.

21. The thigh compression system of claim 14 wherein a plurality of the multiple welds restrict expansion of the bladder.

22. The thigh compression system of claim 14 wherein the inflation device includes a regulator which controls the pressure of a pressurized air or oxygen source.

23. The thigh compression system of claim 22 wherein the regulator includes a diaphragm that is at least 1 inch in diameter.

24. The thigh compression system of claim 14 further including a quick release connector to provide rapid deflation of the air tight bladder.

25. The thigh compression system of claim 14 wherein, when the thigh compression device is affixed on the thigh of a human patient and inflated to about 50 mmHg, the device reduces the venous flow from the thigh and suppresses enhancement of veins on peripheral MR Angiography.

26. The thigh compression system of claim 14, wherein each edge is defined by one or more edge welds attaching the opposing sides of the bladder, and wherein none of the multiple welds within the bladder extends to any of the edge welds.

27. A method of reducing venous enhancement on peripheral magnetic resonance imaging comprising:
   (a) providing a compression device, the compression device comprising:
      an inflatable, double-sealed bladder shaped as an angular sector of an annulus so that the inflatable bladder has two linear edges and two curved edges, the first curved edge being longer than and having a greater radius of curvature than the second curved edge, the inflatable bladder being capable of snuggly fitting the conical shape of the thigh of a human when the first edge is positioned proximally on the thigh while the second edge is positioned distally on the thigh, the inflatable bladder comprising opposing sides attached to one another in part by multiple round welds spaced 1 to 2 inches apart that avoid ballooning of the inflatable bladder during inflation, the bladder having exactly one port to receive and expel inflation air, the port being located along the first edge;

a bladder pouch disposed around the inflatable bladder;

a tubing having a first end attached to the port and a second end;

a pressure regulator having an output attached to the second end of the tubing, the pressure regulator being capable of maintaining the pressure in the inflatable bladder at a pressure of 60 mmHg;

a high-pressure air reservoir having an output connected to an input of the pressure regulator; and a pressurized air source connected to an input of the high-pressure reservoir, capable of inflating the high-pressure to pressures higher than 60 mmHg;

wherein the entire device is constructed of MR-compatible materials;

(b) securing the compression device to the thigh of a patient so that the first edge and the port are proximal, facing the patient's abdomen, and the second edge is distal, facing the patient's calf;

(c) advancing the patient into an MR scanner feet first so that the tubing extends directly out of the MR scanner without folding back on itself;

(d) uniformly compressing the thigh without substantially displacing the leg or putting the leg into an unstable position by causing air to be admitted from the pressurized air source to the reservoir at a pressure above 60 mmHg, thereby causing air to flow through the regulator and into the bladder, thereby inflating the bladder to 60 mmHg, and thereby slowing venous blood flow in the thigh by compression of veins in the patient's thigh;

(e) obtaining a first 3D gradient echo MR image;

(f) injecting a contrast agent into an arm vein of the patient;

(g) obtaining a second 3D gradient echo MR image using the same imaging parameters for obtaining a first 3D gradient echo MR image;

(h) creating a final image by subtracting the first 3D gradient echo MR image from the second 3D gradient echo MR image: and (i) maintaining a pressure of 60 mmHg within the inflatable bladder during steps (d) through (g) by continuously replenishing air from the reservoir through the regulator into the tubing and into inflatable bladder via the exactly one port whenever the pressure in the inflatable bladder drops below 60 mmHg.

28. A thigh compression system for use with magnetic resonance imaging equipment, the thigh compression system comprising:

a thigh compression device including:

first and second layers of flexible material welded together to form an air tight bladder wherein the bladder has a curved rectangular-like shape including a first side that is longer than an opposing second side, and wherein the bladder is inflatable by air and has exactly one port to receive and expel inflation air, the port being located along the first side of the bladder;

multiple welds within the bladder which restrict the amount that the bladder expands when inflated;

extension tubing coupled to the bladder; and an inflation device, coupled to the extension tubing of the thigh compression device, to inflate the inflatable bladder;

wherein a plurality of the multiple welds are round and spaced 1 to 2 inches apart.

* * * * *